United States Patent [19]
Suzuki et al.

[11] Patent Number: 5,204,997
[45] Date of Patent: Apr. 27, 1993

[54] DISPOSABLE GARMENTS OF PANTS TYPE

[75] Inventors: Migaku Suzuki, Kamakura; Takeshi Kudo, Kawanoe; Ritsuko Sakai; Rumi Yamaki, both of Kakegawa, all of Japan

[73] Assignee: Uni-Charm Corporation, Ehime, Japan

[21] Appl. No.: 899,786

[22] Filed: Jun. 15, 1992

Related U.S. Application Data

[63] Continuation of Ser. No. 704,424, May 23, 1991.

[30] Foreign Application Priority Data

May 24, 1990 [JP] Japan .................. 2-134439

[51] Int. Cl.⁵ .............. A41B 9/00; A41B 9/12; A41B 9/16
[52] U.S. Cl. .................. 2/400; 2/111; 2/112; 2/401; 2/403; 2/406; 2/243 R; 604/365; 604/385.1; 604/385.2
[58] Field of Search .............. 2/111, 112, 400, 401, 2/402, 403, 406, 274, 243 R, 243 B, 237; 604/385.1, 385.2, 365, 394, 396

[56] References Cited

U.S. PATENT DOCUMENTS

| | | |
|---|---|---|
| 1,329,119 | 1/1920 | George . |
| 1,833,960 | 12/1931 | Alsop . |
| 1,998,140 | 4/1935 | Loew . |
| 2,703,085 | 3/1955 | Schmidt . |
| 2,748,772 | 6/1956 | Titone . |
| 2,770,237 | 11/1956 | Starr . |
| 2,977,957 | 4/1961 | Clyne . |
| 3,025,856 | 3/1967 | Burwell . |
| 3,424,162 | 1/1969 | Parravicini . |
| 4,315,508 | 2/1982 | Bolick . |
| 4,642,819 | 2/1987 | Ales . |
| 4,769,023 | 9/1988 | Goebel . |
| 4,771,483 | 9/1988 | Hooreman . |
| 4,771,493 | 9/1988 | Hooreman . |
| 4,819,401 | 6/1974 | Massengale . |
| 4,838,886 | 6/1989 | Kent . |
| 4,904,249 | 2/1990 | Miller . |
| 4,909,802 | 3/1990 | Ahr . |
| 5,061,261 | 10/1991 | Suzuki . |

FOREIGN PATENT DOCUMENTS

| | | |
|---|---|---|
| 0164435 | 12/1985 | European Pat. Off. . |
| 0243013 | 10/1987 | European Pat. Off. . |
| 0345664 | 12/1989 | European Pat. Off. . |
| 282061 | 7/1952 | Fed. Rep. of Germany . |
| 1294232 | 4/1962 | France . |
| 1144674 | 3/1969 | United Kingdom . |
| 2072491 | 10/1981 | United Kingdom . |

Primary Examiner—Clifford D. Crowder
Assistant Examiner—Jeanette E. Chapman
Attorney, Agent, or Firm—Fred Philpitt

[57] ABSTRACT

A disposable garment of pants type, such as a disposable diaper of pants type, is constructed by attaching respective leg-hole surrounding flaps and waist-hole surrounding flaps to respective opposite side edges extending longitudinally of a basic assembly for the garment which comprises at least a topsheet and a backsheet. The leg-hole surrounding flaps and the waist-hole surrounding flaps respectively cooperate to form a pair of leg-holes. A pair of shoulder straps can be easily prepared by making a slit which extends longitudinally of the garment on each waist-hole surrounding flap. A disposable garment of the present invention is featured in its simple construction and easy production.

8 Claims, 6 Drawing Sheets

DISPOSABLE GARMENTS OF PANTS TYPE

This is a continuation of application Ser. No. 07/704,424, filed May 23, 1991 and the benefits of 35USC120 are claimed relative to it.

BACKGROUND OF THE INVENTION

The present invention relates to disposable garments and more particularly to such garments of pants type having a simplified construction.

While most of commonly used disposable garments such as diaper, training pants and incontinence briefs have been of so-called open type, such disposable garments of pants type have been also proposed, for example, by U.S. Pat. No. 4,771,483.

The present invention is directed to disposable garments of pants type having a simplified construction. The above-identified U.S. Pat. No. 4,771,483 also proposes such disposable pants type garments of a simplified construction. According to this prior art, a rectangular sheet material is provided along each of opposite side edges with a single slit extending substantially in parallel to the associated one of said opposite side edges and a narrow section defined between said slit and said associated one of the opposite side edges is incorporated with a suitable elastic member under its stretched condition so as to form a pair of waist-hole surrounding elastic bands. However, this prior art has substantially no regard for prevention of body fluid leakage possibly occurring around the leg-holes, which is critical for the disposable garments in general and, therefore, may raise a problem in practical use. In view of such situation, it is an object of the invention to provide novel disposable garments of pants type allowing said body fluid leakage to be effectively prevented with a simplified construction.

SUMMARY OF THE INVENTION

The object set forth above is achieved, in accordance with the invention, by disposable garments of pants type comprising a basic assembly including at least a liquid-permeable topsheet and a liquid-impermeable backsheet, and elastic bands mounted on said basic assembly for partially surrounding a waist-hole, said basic assembly having outlines traversing respective longitudinally extending opposite side edges and transversely extending opposite end edges, characterized in that each of said opposite side edges is provided with a flap and said elastic band, said flap surrounding a leg-hole cooperatively with said elastic band, an outer side edge of said leg-hole surrounding flap being attached to said basic assembly along the associated one of said opposite side edges thereof, and respective end edges of said leg-hole surrounding flap and said waist-hole surrounding elastic band being attached to said basic assembly by means of respective attaching lines provided along the outline of said garments. These and the other features of the invention will be more apparent from the following description.

According to the present invention, there are provided a pair of leg-hole surrounding flaps extending longitudinally of the garments along the opposite side edges thereof, respectively. Each of said leg-hole surrounding flaps has its outer side edge fluid-tightly attached to the associated one of said opposite side edges of the garments and its inner side edge cooperating with said topsheet of the garments to form a pocket opened towards a center line extending longitudinally of said garments. Said pocket is effective to prevent leakage of body exudate which otherwise might occur around the legs of a wearer. There are further provided a pair of waist-hole surrounding elastic bands extending along said opposite side edges, respectively. These elastic bands are attached to the basic assembly of the garments only at their end edges along the respective outlines of said basic assembly. Accordingly, said garments are excellent in function and very simple in construction, allowing themselves to be easily assembled and to be offered to users at a reasonably low cost.

PREFERRED EMBODIMENTS OF THE INVENTION

The invention will be described more in detail with reference to the accompanying drawings. It should be understood that each disposable diaper of the embodiment is laterally symmetric with respect to a center line extending longitudinally thereof.

Embodiment 1

Figure 1:
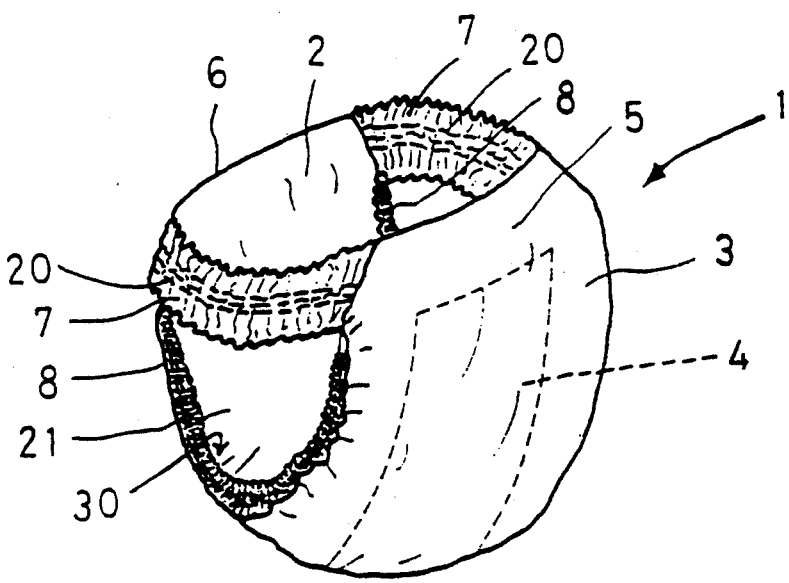
FIG. 1 is a perspective view illustrating disposable diaper of pants type as one embodiment of the present invention.
Figure 2:
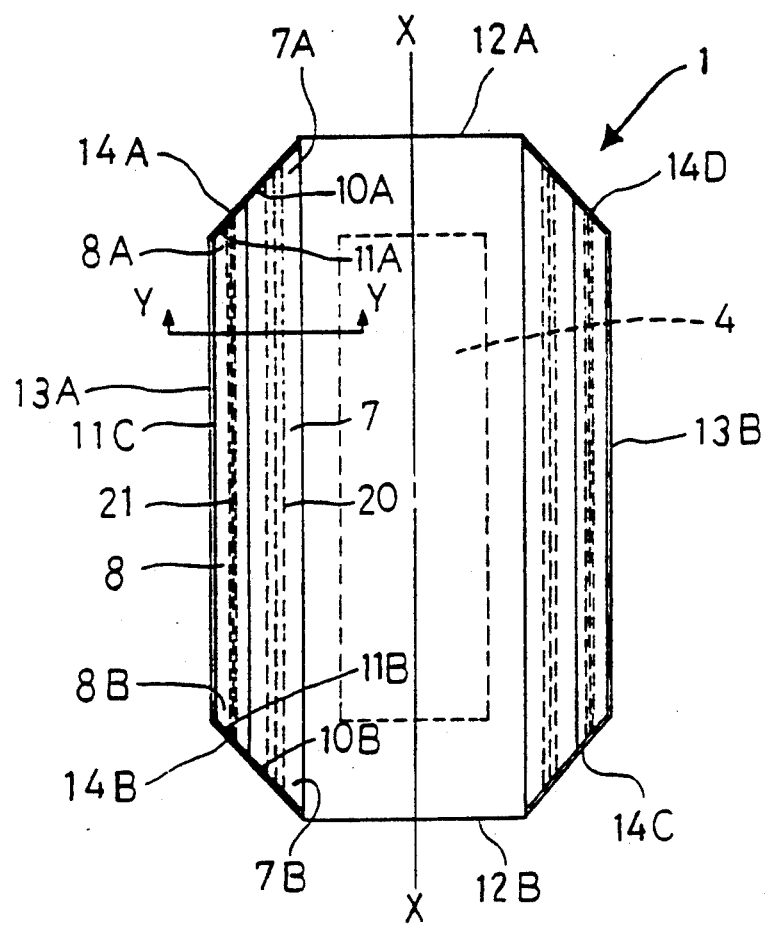
FIG. 2 is a plan view of the same.

FIG. 1 is a perspective view of so-called pants type disposable diaper 1 constructed as a specific embodiment of the invention and FIG. 2 is a plan view of the same diaper 1 as being longitudinally stretched and developed to a flat position with its inner side facing upwards. Since the diaper 1 is laterally symmetric with respect to the center line extending longitudinally, as has previously been mentioned, only the left half of the diaper as viewed in FIG. 2 will be described in detail.

Referring to FIG. 1, the diaper 1 comprises a basic assembly constructed of a water-permeable topsheet 2, a water-impermeable backsheet 3 and an absorbent core 4 sandwiched therebetween, a pair of waist-hole surrounding elastic bands 7 connecting a front body 5 to a rear body 6 in said basic assembly, and a pair of leg-hole surrounding flaps 8. Each of the waist-hole surrounding elastic bands 7 has a plurality of rubber strips 20 and each of the leg-hole surrounding flaps 8 also has a plurality of rubber strips 21, both being made in the form of elastic gathers. Both the waist-hole surrounding elastic band 7 and the leg-hole surrounding flap 8 comprise water-impermeable materials and, more preferably, air-permeable but water-impermeable materials such as nonwoven fabric formed from suitable hydrophobic fibres.

Now referring to FIG. 2, the leg-hole surrounding narrow flaps 8 extend along opposite side edges of the diaper 1, respectively, each of said flaps 8 having its outer side edge attached to the topsheet 2 or the backsheet 3 of the basic assembly along a bonding line 11C and its inner side edge opposed to the outer side edge of the associated waist-hole surrounding elastic band 7. The flap 8 has its longitudinally opposite ends 8A, 8B attached to the topsheet 2 or the backsheet 3 along respective attaching lines 11A, 11B and, similarly, the elastic band 7 has its longitudinally opposite ends 7A, 7B attached thereto along respective attaching lines 10A, 10B, said attaching lines 11A, 10A and 11B, 10B extending along respective outlines 14A, 14B of the basic assembly, as will be described later more in detail. The attaching lines 10A, 10B, 11A, 11B and 11C are formed by well known means such as adhesion and hot melt welding, of which at least the lines 11A through 11C are respectively required to be continuous to prevent leakage of body exudate possibly occurring around the user's legs. Thus, a pocket 30 opened towards the center line X—X is cooperatively defined. Additionally, it is preferred that the respectively adjacent lines 10A, 11A and 10B, 11B are continuous into respective single lines in order to achieve a neat appearance of area accompanied by these lines.

The lines 10A, 11A are provided along a straight line 14A corresponding to an outline traversing a longitudinal end edge 12A and a side edge 13A of the basic assembly while the lines 10B, 11B are provided along a straight line 14B corresponding to an outline section traversing the other end edge 12B and said side edge 13A. In this manner, the waist-hole surrounding elastic band 7 is adapted to have a natural fitness around the associated side of the wearer's waist (not shown), as will be apparent from FIG. 1.

Figure 2A:
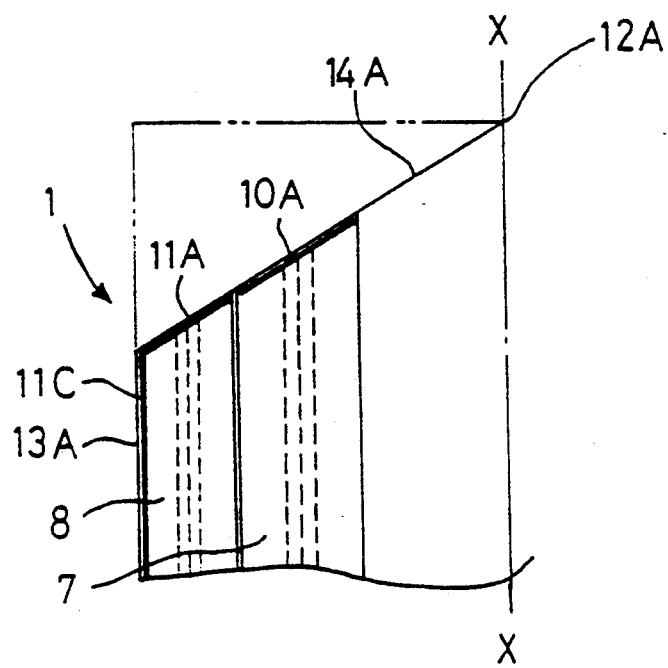
FIGS. 2A through 2C are fragmentary plan views illustrating by way of example how the end edge is attached along the outline of the garments.

Referring to FIG. 2A, there is illustrated another embodiment of the above-mentioned attaching, in which said straight line 14A corresponds to an outline connecting an intersecting point of the end edge 12A and the longitudinally extending center line X—X to the side edge 13A. In this embodiment, the opposite end edges of the basic assembly are substantially defined by the points 12A, 12B, respectively, and such configuration also is covered by the scope of the present invention.

Figure 2B:
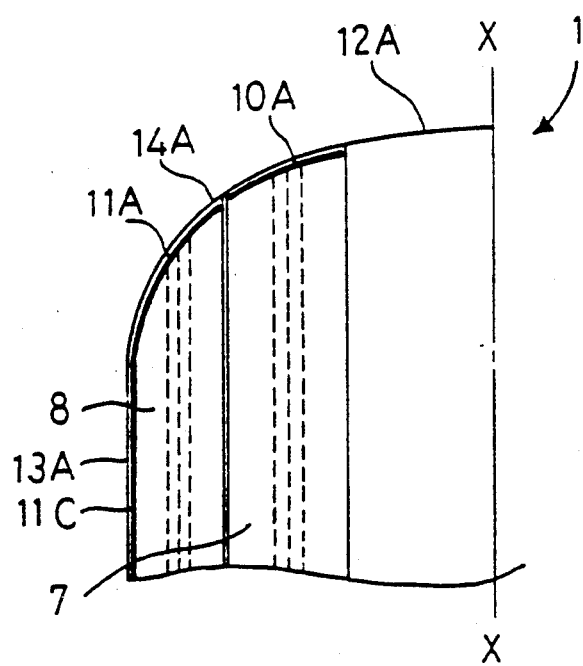

FIG. 2B illustrates still another embodiment of the above-mentioned attaching, in which said straight line 14A corresponding to said outline is replaced by a curved line. Such configuration also is covered by the scope of the present invention.

Figure 2C:
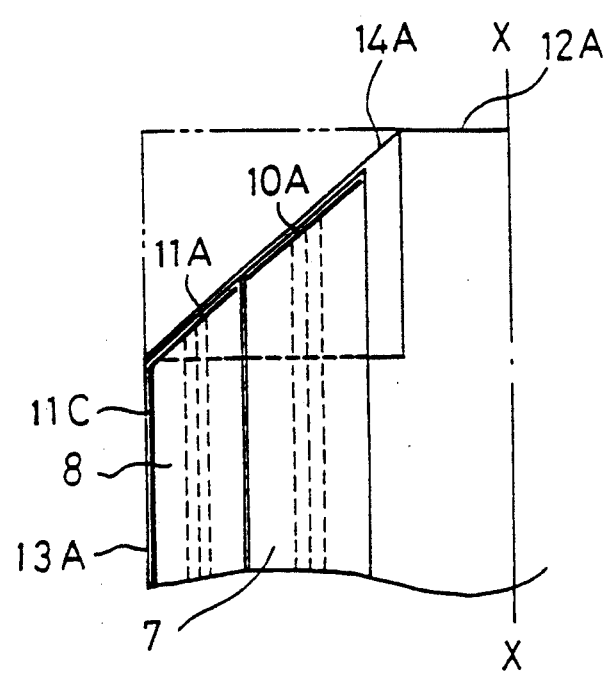

FIG. 2C illustrates further another case in which said straight line 14A corresponding to said outline is formed by folding a corner zone defined between the end edge 12A and the side edge 13A back inwards. In this case the topsheet 2 can be fixed in face-to-face relationship by means of adhesion in order to avoid any undesirable displacement thereof. The waist-hole surrounding elastic band 7 and the leg-hole surrounding flap 8 are respectively attached to the backsheet 3 at said folded corner zone by the attaching lines 10A, 11A extending along the straight line 14A.

Figure 3A:
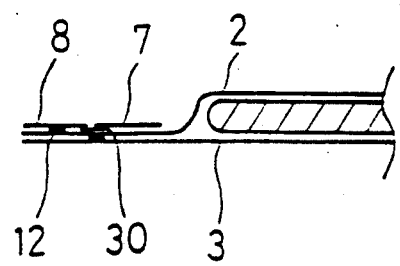
FIGS. 3A through 3C are sectional views taken along a line Y—Y in FIG. 2 and illustrate by way of example manners of said edge attaching.
Figure 3C:
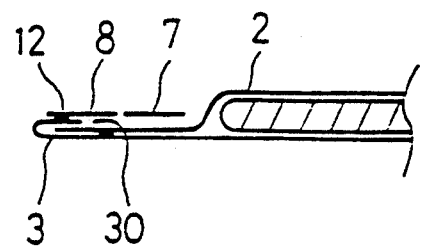
Figure 3B:
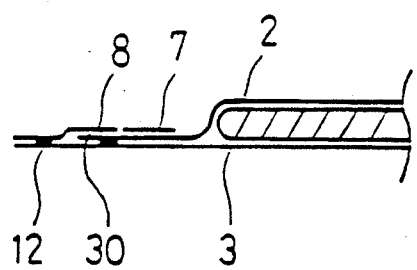

FIGS. 3A through 3C and FIGS. 4A and 4B illustrate further various variations of the above-mentioned attaching. FIGS. 3A, 3B and 3C schematically illustrate how the flap 8 is attached along the side edge thereof to the basic assembly of the diaper 1 in a sectional view as taken between arrows Y—Y in FIG. 2 and viewed in the direction of these arrows. Specifically, FIG. 3A illustrates a case in which the flap 8 is attached to the topsheet 2 by means of hot melt adhesive 12, FIG. 3B illustrates a case in which the flap 8 is attached to the backsheet 3 extending outwards from the outer side edge of the topsheet 2, and FIG. 3C illustrates a case in which the said backsheet 3 extending outwards from the side edge of the topsheet 2 in FIG. 3B is folded back inwards and the flap 8 is attached over this folded edge. The manners of attaching as illustrated by FIGS. 3B and 3C are advantageous in that a body exudate having permeated through the water-permeable topsheet 2 is having permeated through the water-permeable topsheet 2 is dammed up within the pocket 30 and effectively prevented from exuding through the side edges of the diaper 1.

Attaching may be effected along the opposite side edges and the respective outlines of the basic assembly in the manners as have been described above to form the diaper 1 illustrated by FIG. 2. The rubber strips 20 associated with the waist-hole surrounding elastic band 7 and the rubber strips 21 associated with the leg-hole surrounding flap 8 have previously been bonded under their stretched conditions to said elastic band 7 and said flap 8, respectively so that, when the diaper 1 is free from any external force exerted thereon, respective said rubber strips contract to form gathers in the elastic band 7 and the flap 8 while the inner side edge of said flap 8 more or less tends to rise and to form the pocket 30 in cooperation with the topsheet 2.

While this specific embodiment has been illustrated as including the absorbent core 4, the absorbent core 4 is not essential to the present invention.

Embodiment 2

Figure 4:
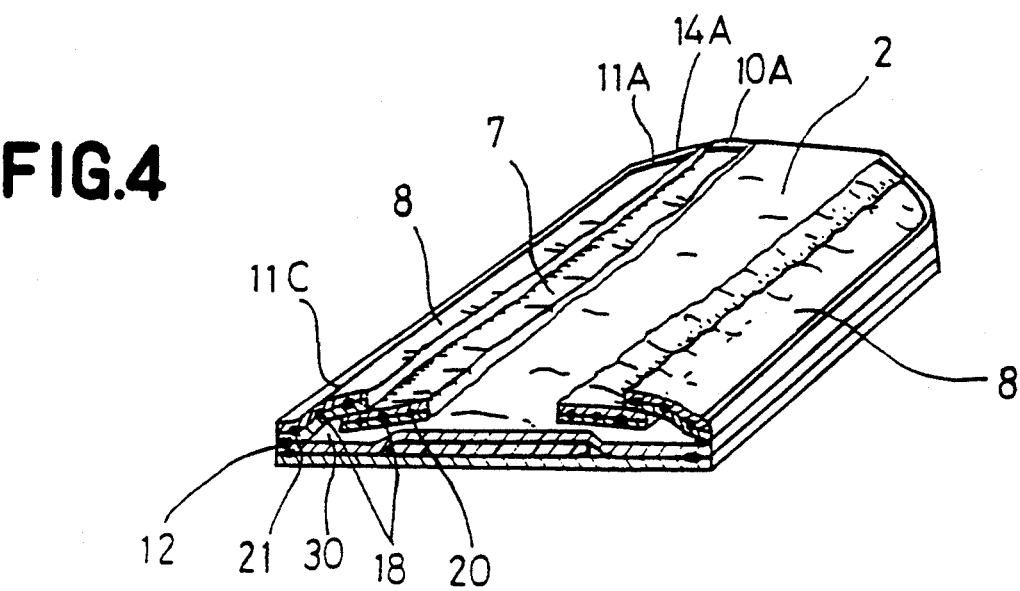
FIG. 4 is a perspective view illustrating, partially in a section, an example of overlap attaching of the end edge.

FIG. 4 illustrates another embodiment of the invention partially in a transverse section. This embodiment is similar to Embodiment 1 except that the waist-hole surrounding elastic band 7 overlaps the associated leg-hole surrounding flap 8 so that the elastic band 7 is partially interposed between the flap 8 and the topsheet 2. In this embodiment, the attaching line 10A for the elastic band 7 and the attaching line 11A for the flap 8 both extending along the straight line 14A corresponding to an outline of the basic assembly substantially define together a single continuous bonding line. With such arrangement, the elastic band 7 underlying the flap 8 lifts the flap 8 off from the topsheet 2 around the lines 10A, 11A as a user widely separates the elastic band 7 and the associated flap 8 to wear the diaper 1, and thereby the pocket 30 is widely opened.

As will be readily understood from FIG. 4, the rubber strips 20, 21 are covered with respective backing sheets 18 so that a wearer's skin is protected against direct contact with these rubber strips 20, 21.

Embodiment 3

Figure 5:
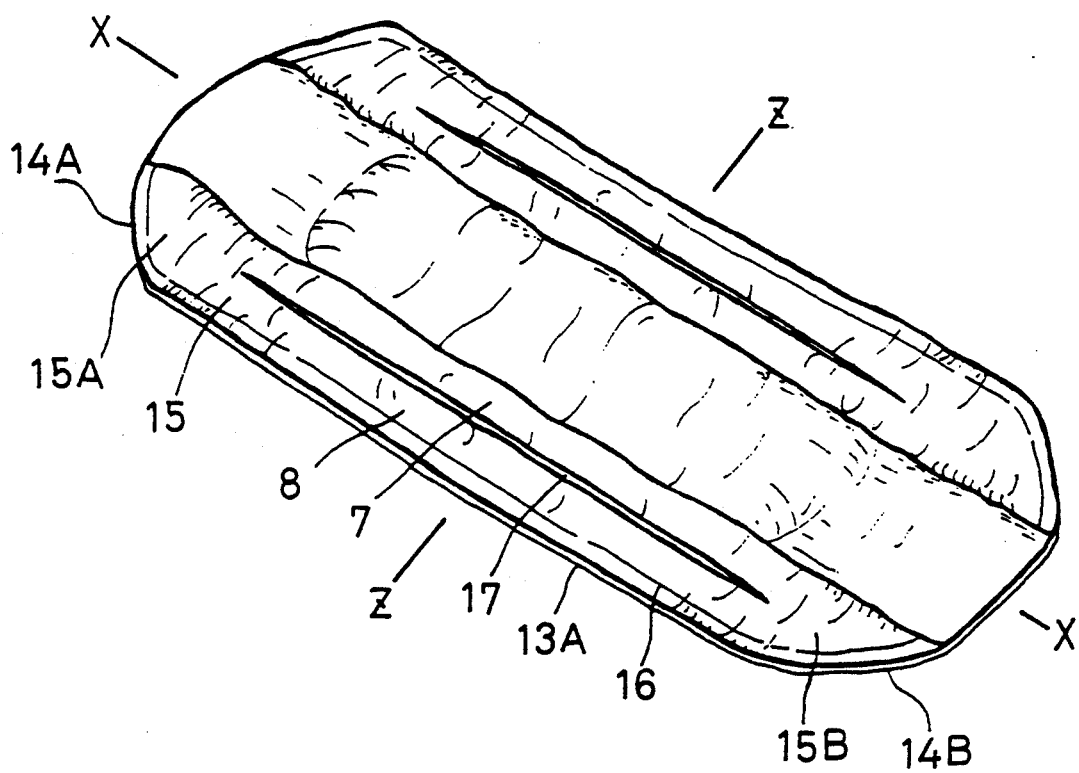
FIGS. 5 and 6 are a perspective view and a perspective view partially in section taken along a line Z—Z in FIG. 5, respectively, illustrating another embodiment of the invention.

FIG. 5 illustrates a specific embodiment in which the waist-hole surrounding elastic band 7 and the associated leg-hole surrounding flap 8 are integral with each other. A water-impermeable, preferably air-permeable but water-impermeable sheet member 15 is attached to the topsheet 2 along each of the opposite side edges thereof by an attaching line 16 made of hot melt adhesive 12 and said attaching line 16 extends to the opposite end edges of the diaper 1 so as to attach opposite end edges 15A, 15B of said sheet member 15 also to the topsheet 2. The sheet member 15 is formed with a slit 17 extending longitudinally thereof so that said slit 17 divides the sheet member 15 into the waist-hole surrounding elastic band 7 on the side of said center line X—X extending longitudinally of the diaper 1 and the leg-hole surrounding flap 8 on the side of the side edge 13A, said elastic band 7 and flap 8 being integral with each other at opposite ends of said slit 17.

Figure 6:
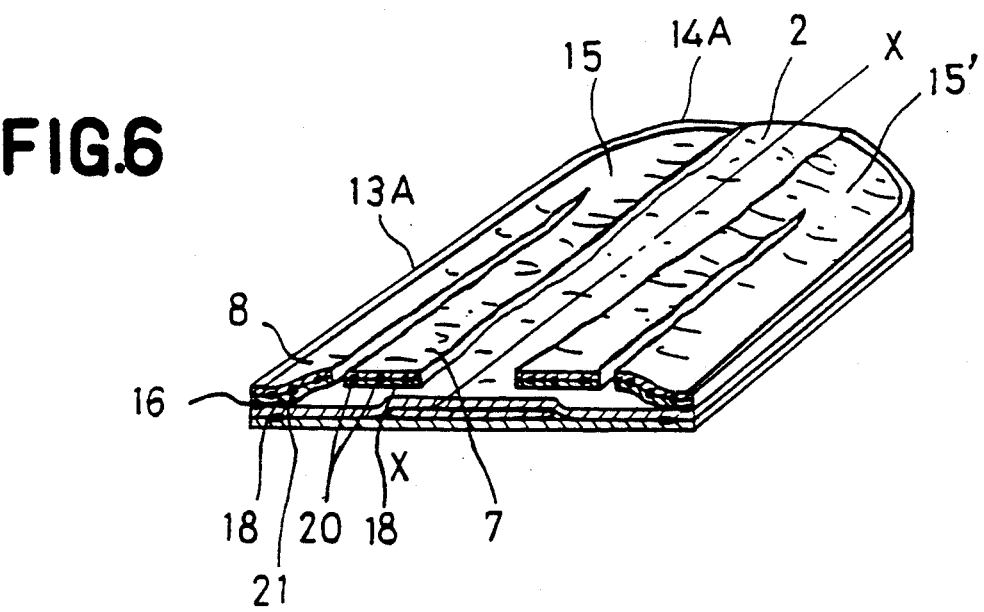

FIG. 6 illustrates a section taken along a line Z—Z in FIG. 5. As illustrated, the elastic band 7 is incorporated with the rubber strips 20 and the flap 8 is incorporated with the rubber strips 21. It is not critical for the present invention whether the rubber strips 20, 21 are same or not in their material, configuration, number or amount, elongation percentage and the other factors.

Embodiment 4

Figure 7:
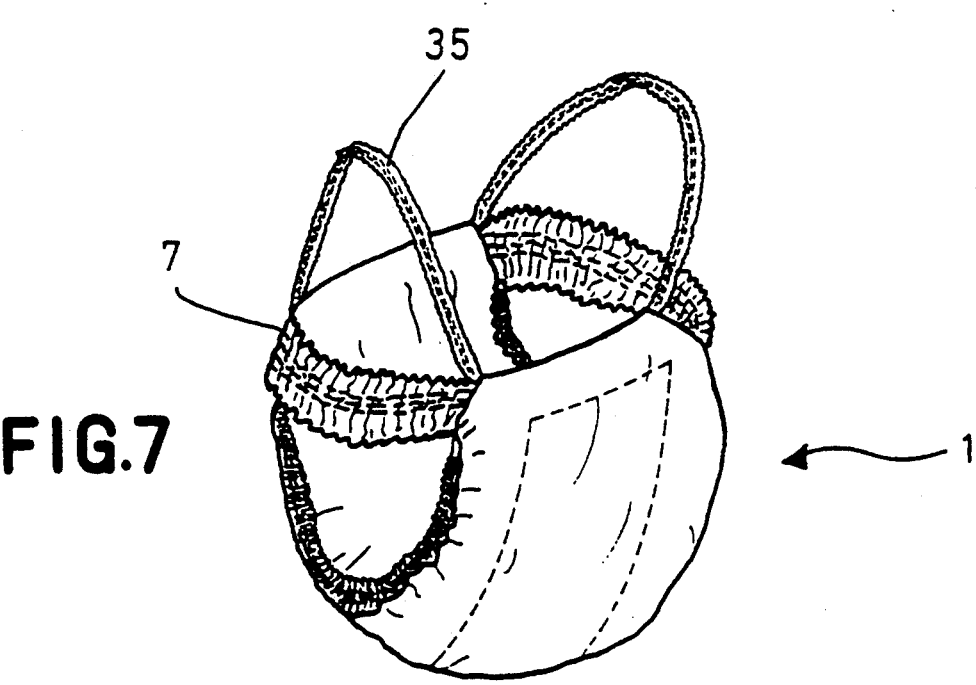
FIGS. 7 and 8 are a perspective view and a fragmentary plan view illustrating still another embodiment of the invention.

FIG. 7 illustrates a case in which each of the waist-hole elastic bands 7 provides a shoulder strap 35.

Figure 8:
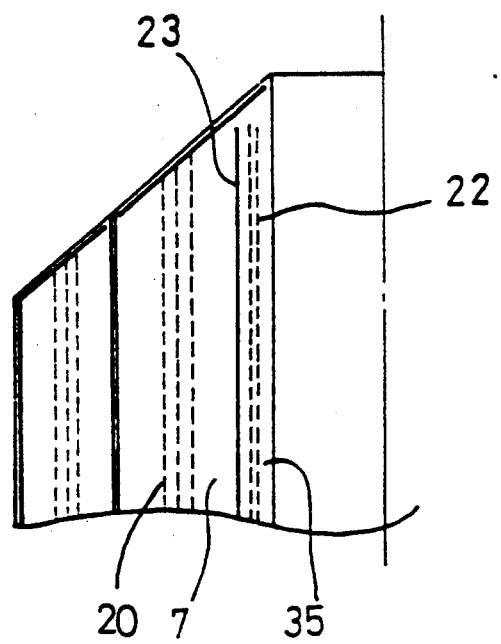

FIG. 8 illustrates the diaper 1 as stretched and developed to its flat position. As seen in FIG. 8, the waist-hole elastic band 7 is provided with a longitudinal slit 23 so that a narrow portion of the elastic band 7 defined between the inner side edge thereof and the slit 23 can be used as a shoulder strap 35. The shoulder strap 35 may be incorporated with appropriate number of rubber strips 22 as indicated by broken lines, if desired, and these rubber strips 22 may be bonded to the shoulder strap 35 simultaneously when the rubber strips 20 are bonded to the elastic band 7. It is not critical for the invention whether the rubber strips 20, 22 are similar or not.

What is claimed is:

1. A disposable garment of the pants type comprising a basic assembly including at least a liquid-permeable topsheet (2) and a liquid-impermeable backsheet (3), and elastic bands (7) mounted on said basic assembly for partially surrounding a waist-hole, said basic assembly having outlines traversing longitudinally extending opposite side edges (13A, 13B) and transversely extending opposite end edges (12A, 12B) characterized in that each of said opposite side edges (13A, 13B) is provided with a flap (8) and said elastic band (7), said flap (8) surrounding a leg-hole cooperatively with said elastic band (7), an outer side edge of said leg-hole surrounding flap (8) being attached to said basic assembly along one of said opposite side edges (13A, 13B) and end edges (8A, 8B, 7A, 7B) of said leg-hole surrounding flap (8) and said waist-hole surrounding elastic band (7) being attached to said basic assembly by means of bonding lines (10A, 11A, 10B, 11B) provided along the outlines of said garment, said leg-hole surrounding flap (8) and said waist-hole surrounding elastic band (7) overlapping each other at least on said bonding lines (10A, 11A, 10B, 11B) and adjacent thereto with said elastic band (7) being interposed between said leg-hole surrounding flap (8) and said topsheet (2).

2. A disposable garment of the pants type comprising a basic assembly including at least a liquid-permeable topsheet (2) and a liquid-impermeable backsheet (3), and elastic bands (7) mounted on said basic assembly for partially surrounding a waist-hole, said basic assembly having outlines traversing longitudinally extending opposite side edges (13A, 13B) and transversely extending opposite end edges (12A, 12B) characterized in that each of said opposite side edges (13A, 13B) is provided with a flap (8) and said elastic band (7), said flap (8) surrounding a leg-hole cooperatively with said elastic band (7), an outer side edge of said leg-hole surrounding flap (8) being attached to said basic assembly along one of said opposite side edges (13A, 13B) and end edges (8A, 8B, 7A, 7B) of said leg-hole surrounding flap (8) and said waist-hole surrounding elastic band (7) being attached to said basic assembly by means of bonding lines (10A, 11A, 10B, 11B) provided along the outlines of said garment, each leg-hole surrounding flap (8) and its adjacent waist-hole surrounding elastic band (7) is formed by providing a single member with a slit.

3. A disposable garment of the pants type as recited in claim 1 wherein said waist-hole surrounding elastic band (7) is provided with a longitudinal slit therein so as to form a shoulder strap (35).

4. A disposable garment of the pants type as recited in claim 2 wherein said waist-hole surrounding elastic band (7) is provided with a longitudinal slit therein so as to form a shoulder strap (35).

5. A disposable garment of the pants type comprising in combination
   (a) a basic assembly that includes at least a liquid-permeable topsheet (2) and a liquid impermeable backsheet (3), outlines of said basic assembly being defined by opposite end edges (12A, 12B) and opposite side edges (13A, 13B),
   (b) leg hole flaps (8) extending inwardly from said side edges (13A, 13B), and overlying said basic assembly when the basic assembly is in a flattened condition, the outer side edges of said flaps (8) being attached to said basic assembly along said opposite side edges (13A, 13B) the inner side edges of said flaps (8) being free from said basic assembly so as to form a pocket (30) in cooperation with the topsheet (2) of said basic assembly, said flaps (8) having end edges (8A, 8B) which are joined to said basic assembly adjacent said opposite end edges (12A, 12B) of said basic assembly, and
   (c) waist hole bands (7) extending inwardly from said leg hole flaps (7) and also overlying said basic assembly when the basic assembly is in a flattened condition, the end edges (7A 7B) of said waist hole bands (7) being joined to said basic assembly adjacent said opposite end edges (12A, 12B) of said basic assembly, the outer side edges of said bands (7) being unattached to said basic assembly so that the unattached inner sides of said flaps (8) and the unattached outer sides of said bands (7) cooperate to form leg hole openings.

6. A disposable garment according to claim 5 wherein said leg hole flaps (8) contains rubber strips (21) which are attached under stretched condition.

7. A disposable garment of the pants type as recited in claim 5 wherein said attaching lines for the end edges (7A, 7B, 8A, 8B) of said leg-hole surrounding flap (8) and associated said waist-hole surrounding elastic band (7) to said basic assembly define a substantially continuous single line (14A, 14B).

8. A disposable garment as recited in claim 5 wherein each waist hole band (7) and leg-hole flap (8) is formed by providing a single member with a slit.

* * * * *